US00PP33487P2

(12) United States Plant Patent
Hansen

(10) Patent No.: US PP33,487 P2
(45) Date of Patent: Sep. 14, 2021

(54) ***PHLOX* PLANT NAMED 'BABY DOLL WHITE'**

(50) Latin Name: ***Phlox* hybrid**
Varietal Denomination: Baby Doll White

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,103

(22) Filed: Sep. 30, 2020

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

(56) References Cited

PUBLICATIONS https://www.facebook.com/marketplace/item/242570727079832/; Sep. 13, 2021 to Sep. 19, 2021; 1 page.*

* cited by examiner

*Primary Examiner* — Kent L Bell

(57) ABSTRACT

A new and unique cultivar of garden *Phlox* named *Phlox* 'Baby Doll White' multiple-branched, multi-stemmed, short, dense, upright, slowly-spreading habit with clean, glossy, medium-green, lanceolate leaves with exceptiond powdery mildew resistance. Foliage is thick with stiff sterns. Flowers are white initially with pale-lavender blush and small, pale-lavender throat and pale-purple corolla tube produced on branched peduncles and nearly cover the top of the plant beginning early June for about four weeks, about two weeks prior to typical *Phlox paniculata* cultivars known to the inventor, and repeating for about six weeks. 'Baby Doll White' is especially suitable as a potted plant, for the garden, for attracting hummingbirds and butterflies, and for cut flower arrangements.

1 Drawing Sheet

Botanical classification: *Phlox* hybrid.
Variety denomination: 'Baby Doll White'.

STATEMENT REGARDING PRIOR DISCLOSURES UNDER 37 CFR 1.77(b)(6)

The first disclosure, in the form of a sale, was made by Walters Gardens, Inc. on Jun. 29, 2020 to Full Circle Gardens. Prior to this sale, Walters Gardens, Inc. featured the new plant on their website with a non-enabling description and photograph on Feb. 1, 2020. Walters Gardens, Inc. obtained the new plant and all information relating thereto, from the inventor. No plants of *Phlox* 'Baby Doll White' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Baby Doll White' and will be referred to hereafter by its cultivar name or the "new plant". The new plant was the result of a controlled hybridization on Nov. 18, 2013 between 'Amethyst Pearl' U.S. Plant Pat. No. 28,487 as the female or seed parent and *Phlox carolina* 'Lil' Cahaba' (not patented) as the male or pollen parent at a wholesale perennial nursery in Zeeland, Mich. The seed was collected in the winter of 2014. During the trial process the new plant was identified by the breeder code 14-17-3. 'Baby Doll White' has been asexually propagated by tip and basal stem cuttings in the greenhouses at the same nursery in Zeeland, Mich. since 2016. The unique characteristics of the new plant have been found to be reproducible and stable in successive generations of asexually propagated plants and the resultant plants have been found to be identical to the original selection.

BRIEF SUMMARY OF THE PLANT

*Phlox* 'Baby Doll White' is unique from its parents and all other tall garden *Phlox* or other hybrid *Phlox* known to the inventor. The new plant differs from the female parent in that the female parent is taller and has different colored flowers. The most closely comparison cultivars known to the inventor are *Phlox* 'Opening Act White' U.S. Plant Pat. No. 27,461, 'Baby Doll Pink' U.S. Plant Pat. No. 32,025, 'Minnie Pearl' (not patented) and 'Opening Act Pink-a-Dot' U.S. Plant Pat. No. 31,732. 'Opening Act White' is much taller in habit and has more white flowers without the pale purple eyes. 'Baby Doll Pink' has flowers that are bright pink with a white halo around a center pink eye zone. 'Opening Act Pink-a-Dot' has a taller habit with smaller, light lavender-pink flowers. 'Minnie Pearl' is slightly taller with a broader more rampant growing habit.

'Amethyst Pearl U.S. Plant Pat. No. 28,487 has light amethyst-pink flowers and taller habit. 'Lil' Cahaba' has flowers that are magenta and the foliage is narrower on a plant with a taller habit. 'Baby Doll White' differs from all other *Phlox* cultivars known to the inventor in the following repeatedly observed traits in combination:

1. Plants of short, dense, rounded habit, slowly spreading by short rhizomes, producing clean, glossy, medium-green, lanceolate leaves;
2. Showing exceptional powdery mildew resistance;
3. Multiple branched, stems produce rounded mounds of flowers starting early in the season;
4. Flower on strong stiff stems of about 33.0 cm tall producing white flower faces with initial, faint, pale-lavender blush, small pale-lavender throat and pale-purple corolla tube;
5. Flowers cover nearly the entire top of the plant;
6. Flowering beginning in early-summer about two weeks prior to typical *Phlox paniculata* cultivars and re-blooming into fall.

BRIEF DESCRIPTION OF THE DRAWINGS

The photographs of the new plant demonstrate the unique traits of 'Baby Doll White' and the overall appearance of the plant at two-years-old grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
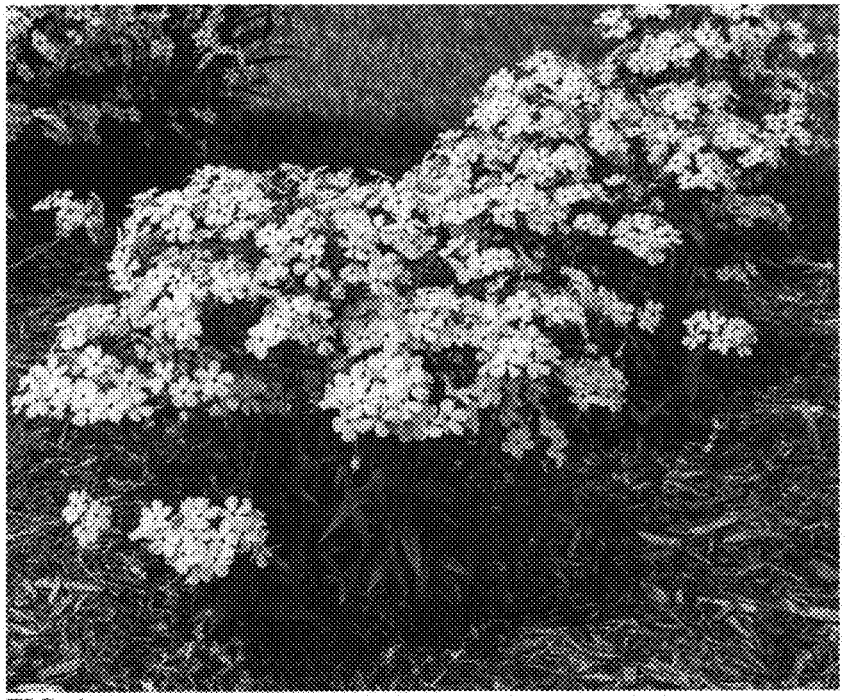
FIG. 1 shows the new plant in peak flower in the landscape.
Figure 2:
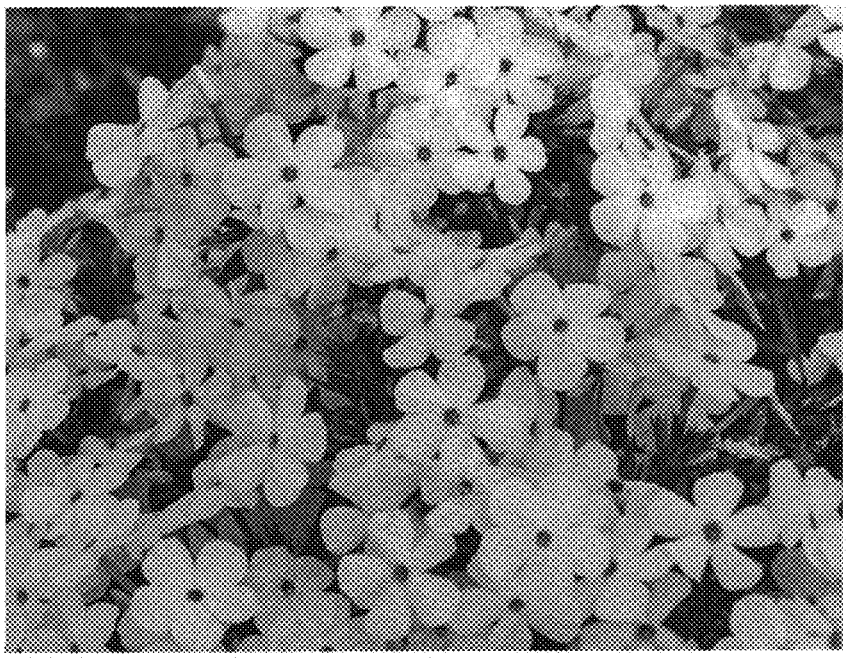
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Baby Doll White' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid;

Parentage: Female or seed parent is 'Amethyst Pearl'; male or pollen parent is 'Lil' Cahaba';

Plant habit: Hardy herbaceous perennial, densely upright, producing about 40 rigid upright stems; flowering about 30.0 cm tall and about 43.0 cm wide; flowering begins early summer in Michigan and continuing for about 4 weeks with repeating for about 6 weeks in late summer;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, lanceolate; entire margin on mature and young leaves; narrowly acute apex; cuneate base;

Leaf size: To about 100.0 mm long by about 27.0 mm wide, average about 70.0 mm long by about 23.0 mm wide;

Leaf surfaces: Glabrous adaxial and adaxial; lustrous adaxial and matte abaxial;

Leaf color expanding: Adaxial between RHS 144A and RHS 144B, abaxial between RHS 146D and RHS 145A;

Leaf color at flowering: Adaxial nearest RHS NN137B, abaxial nearest RHS 146B;

Foliage fragrance: None detected;

Veins: Pinnate; glabrous abaxial and adaxial; midrib about 1.0 mm wide at base, slightly sunken adaxial and raised abaxial;

Vein color: Adaxial midrib nearest RHS 146D, abaxial midrib nearest RHS 145C proximally and distally nearest RHS 146D; secondary adaxial and abaxial veins same color as surrounding leaf;

Petiole: Leaves sessile to 2.0 mm long and 3.0 mm wide; glabrous; flattened;

Petiole color where present: Adaxial nearest RHS 146D, abaxial nearest RHS 145D;

Stems: About 30 per plant; cylindrical; stiff; wiry; strong; upright; glabrous; to about 33.0 cm, average about 28.0 cm long and 4.0 mm diameter at base; lightly branched with cylindrical branches to about 21.0 cm long and 2.0 mm diameter;

Stem color: Nearest RHS 146D with an occasional light blush of nearest RHS N79A proximally;

Nodes: About seven per stem below flowers; average internode length about 4.3 cm;

Node color: Nearest RHS 146D;

Inflorescence: A loosely-branched compound corymb of about 60 flowers on the main stem and about 100 flowers with branches; flowering portion about 11.0 cm long and 9.0 cm across;

Flowers: Perfect; complete; actinomophic; salverform with flat face and long fused tube; typically with five petals; about 25.0 mm long total with tube portion about 23.0 mm long; face about 25.0 mm across; attitude upright to slightly outward; self-cleaning;

Flower longevity: Individually about 5 days on plant or as cut flower;

Flower fragrance: None detected;

Buds one to two days prior to opening: Narrowly oblanceolate, to nearly clavate; acute apex with petals twisted about each other; base fused; about 19.0 mm long and 2.5 mm diameter in tube and swollen to 4.0 mm diameter toward apex bulb of convolute petals;

Bud color: Bulb portion nearest RHS N155B and lightly blushed with RHS 76D, tube portion blend between RHS 76D and RHS N77D;

Petals: Five; margin entire; apex rounded; base fused into tube; adaxial and abaxial limb glabrous, adaxial tube glabrous except pubescent in region about 2.0 mm to 4.0 mm from base, abaxial tube surface glabrous; limbs slightly imbricate about 20 percent over the next petal;

Petal size: Limb to about 11.0 mm wide and about 12.0 mm long, corolla tube to about 23.0 mm long and 2.5 mm diameter at limb;

Petal color: (Young) adaxial limb nearest RHS NN155D and blushed lightly with RHS 76D; abaxial limb nearest RHS NN155D and blushed lightly with RHS 76D; adaxial corolla tube striated longitudinally nearest a blend of RHS N77D and RHS 76D; abaxial corolla tube nearest RHS N77D with basal 3.0 mm of abaxial and adaxial corolla tube nearest RHS 145C;

Petal color: (Mature) adaxial limb nearest RHS NN155D, center eye lightly blushed with nearest RHS 77B extending up to 1.0 mm from throat; abaxial limb nearest RHS NN155D with very faint blushing of nearest RHS 76D; adaxial throat between RHS 77A and RHS 77B lightening proximally to the basal 3.0 mm of corolla tube nearest RHS 155A; abaxial corolla tube striated longitudinally with nearest RHS 77A and RHS NN155C gradually lightening to RHS 155A in basal 3.0 mm;

Androecium: Five;

*Filaments.*—Five; adnate to adaxial corolla tube except free in terminal 1.0 mm; varying lengths between 17.0 mm and 21.0 mm, less than 0.5 mm in diameter; white, nearest RHS NN155D.

*Anther.*—Five; oblong elliptic; basifixed; longitudinal; about 2.5 mm long by 0.7 mm wide; color nearest RHS 13A.

*Pollen.*—Abundant; color nearest RHS 15A.

Gynoecium: One pistil per flower; to about 23.0 mm long;

*Style.*—Cylindrical; about 20.0 mm long and about 0.2 mm diameter; color nearest RHS 2D.

*Stigma.*—Exserted; trifurcate in the distal 1.0 mm, less than 0.25 mm in diameter; persistent after flower abscission; color nearest RHS 10A.

*Ovary.*—Superior; conical; acute apex, base truncate; about 2.0 mm long and 1.0 mm diameter; color nearest RHS 146D and RHS 145B.

Calyx: Tubular; to about 9.0 mm long and 3.0 mm wide at apex;

Sepals; Five; lanceolate; narrowly acute apex, margin entire; fused in the basal 4.0 mm; adaxial and abaxial surface slightly lustrous; individually about 9.0 mm long and 1.0 mm wide;

Sepal color: Adaxial nearest RHS 146B with margins nearest RHS 158D; abaxial variable, proximally nearest RHS 145B, distally RHS N77C and RHS 146B with margins nearest RHS 158D;

Peduncle: Glabrous, stiff, strong, moderately lustrous, upright, cylindrical; to about 31.0 cm long and 2.0 mm diameter at base of flower branches and about 4.0 mm diameter near soil; branches to about 20.0 mm long and 1.0 mm diameter at base;

Peduncle color: Nearest RHS 145B;

Pedicel: Cylindrical; micro-glandular; to about 3.0 mm long and 1.0 mm diameter;

Pedicel color: Nearest RHS 145B;

Fruit and seeds have not yet been observed.

Hardiness and culture: The new plant grows best with plenty of moisture and adequate drainage; hardy to at least from USDA zone 4 through 8.

Disease and pest resistance: *Phlox* 'Baby Doll White' demonstrated the excellent powdery mildew resistance caused by *Erysiphe cichoracearum* under conditions of intense pressure that would normally show symptoms. Past resistance and susceptibility beyond that common for Hybrid *Phlox* has not been observed.

I claim:

1. A new and distinct cultivar of hybrid *Phlox* plant named *Phlox* 'Baby Doll White', as herein described and illustrated.

* * * * *